United States Patent
Smith, III et al.

(10) Patent No.: US 12,343,484 B2
(45) Date of Patent: Jul. 1, 2025

(54) CANNULA FIXATION DEVICE

(71) Applicant: LivaNova USA, Inc., Houston, TX (US)

(72) Inventors: Hubert S. Smith, III, Denver, CO (US); Bryan C. Journey, Superior, CO (US); Francesco Benatti, Concordia (IT)

(73) Assignee: LivaNova USA, Inc., Houston, TX (US)

( * ) Notice: Subject to any disclaimer, the term of this patent is extended or adjusted under 35 U.S.C. 154(b) by 924 days.

(21) Appl. No.: 17/034,821

(22) Filed: Sep. 28, 2020

(65) Prior Publication Data

US 2021/0023342 A1 Jan. 28, 2021

Related U.S. Application Data

(63) Continuation of application No. PCT/US2018/027176, filed on Apr. 11, 2018.

(51) Int. Cl.
*A61M 25/02* (2006.01)
*A61M 1/30* (2006.01)

(52) U.S. Cl.
CPC .............. *A61M 25/02* (2013.01); *A61M 1/30* (2013.01); *A61M 2025/0266* (2013.01); *A61M 2025/0286* (2013.01)

(58) Field of Classification Search
CPC ............. A61M 25/02; A61M 1/30; A61M 2025/0266; A61M 2025/0286; A61M 2025/024; A61M 2039/0223
See application file for complete search history.

(56) References Cited

U.S. PATENT DOCUMENTS

| | | | |
|---|---|---|---|
| 8,734,400 B2 * | 5/2014 | Ciccone | A61M 25/02 604/179 |
| 9,888,909 B2 * | 2/2018 | Gov-Ari | A61B 1/24 |
| 2014/0022810 A1 | 8/2014 | Rosenberg et al. | |
| 2014/0276542 A1 | 9/2014 | Ciccone | |
| 2017/0296788 A1 * | 10/2017 | Andino | A61M 5/1418 |

FOREIGN PATENT DOCUMENTS

| | | |
|---|---|---|
| CN | 105854152 A | 8/2016 |
| FR | 3051118 A1 | 11/2017 |

OTHER PUBLICATIONS

International Preliminary Report on Patentability, dated Oct. 22, 2020 for International Application No. PCT/US2018/027176.

* cited by examiner

*Primary Examiner* — Nathan R Price
*Assistant Examiner* — Fatimata Sahra Diop
(74) *Attorney, Agent, or Firm* — Seager, Tufte & Wickhem LLP

(57) ABSTRACT

A cannula fixation device includes a base having a platform; a subject-interface portion having an upper surface and a lower surface, the upper surface coupled to the base and the lower surface configured to be coupled to a subject; and a clip assembly configured to retain a portion of a cannula. The clip assembly is moveably coupled to the base such that the clip assembly can be selectively positioned in a first position relative to the base or a second position relative to the base.

18 Claims, 9 Drawing Sheets

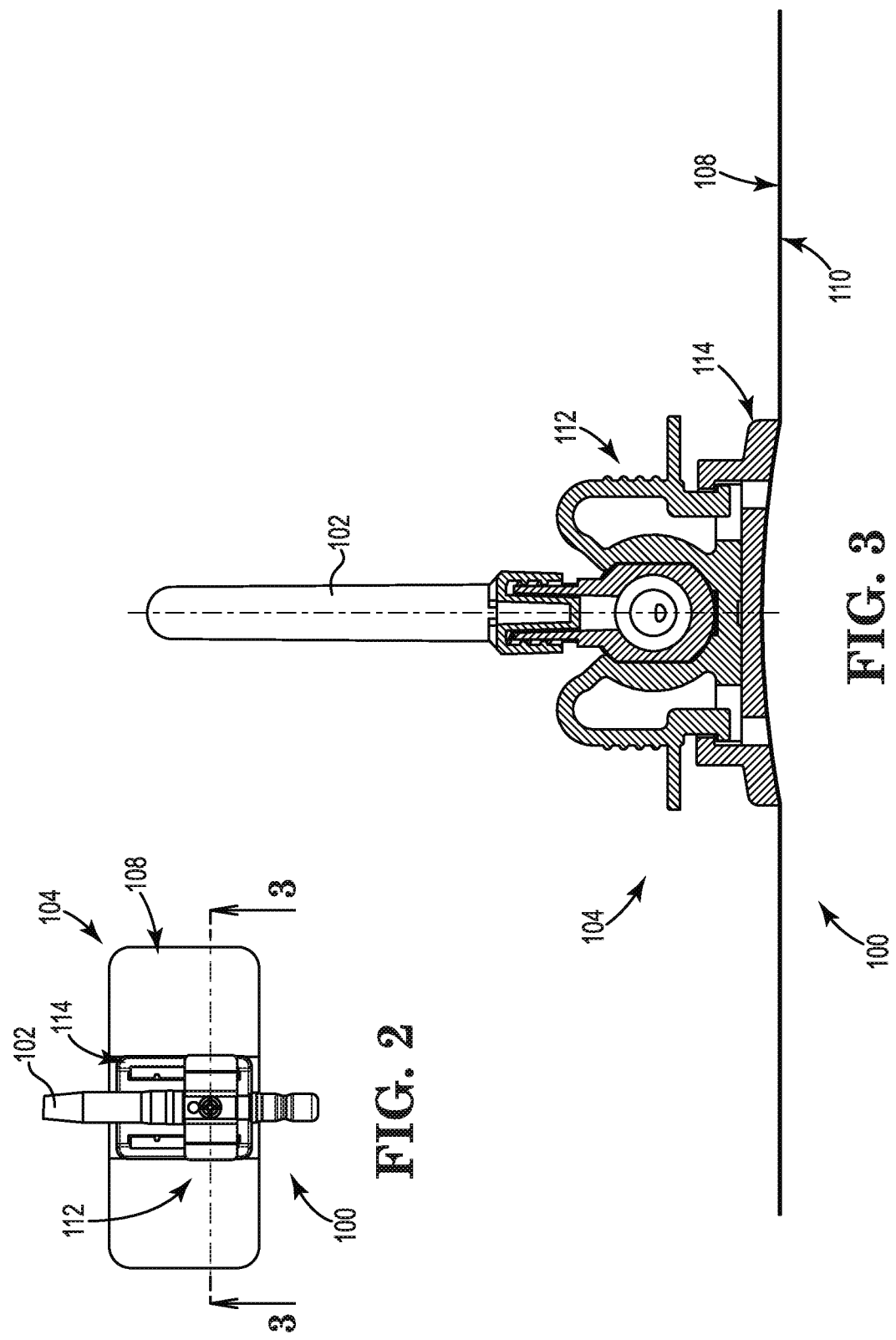

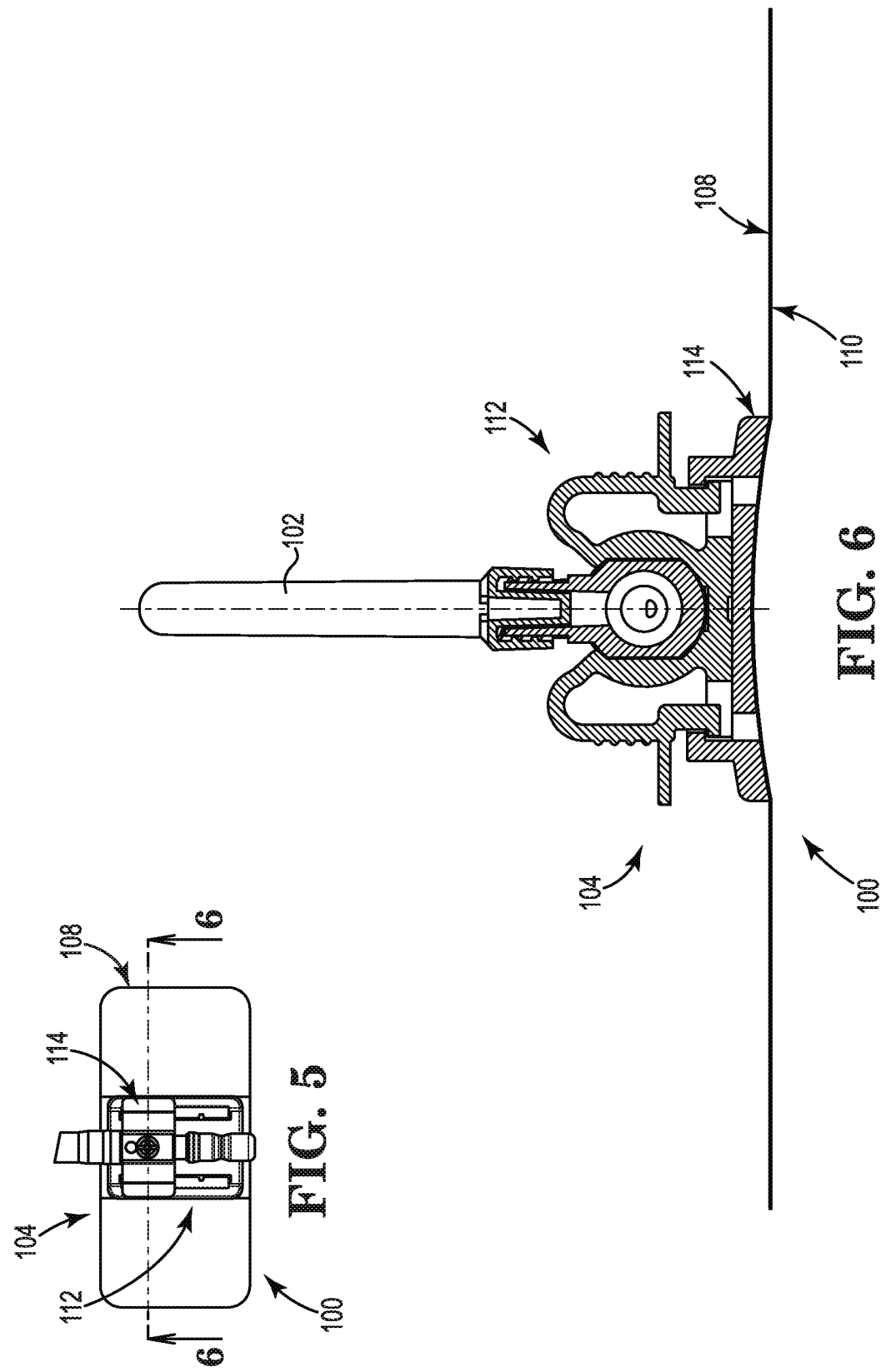

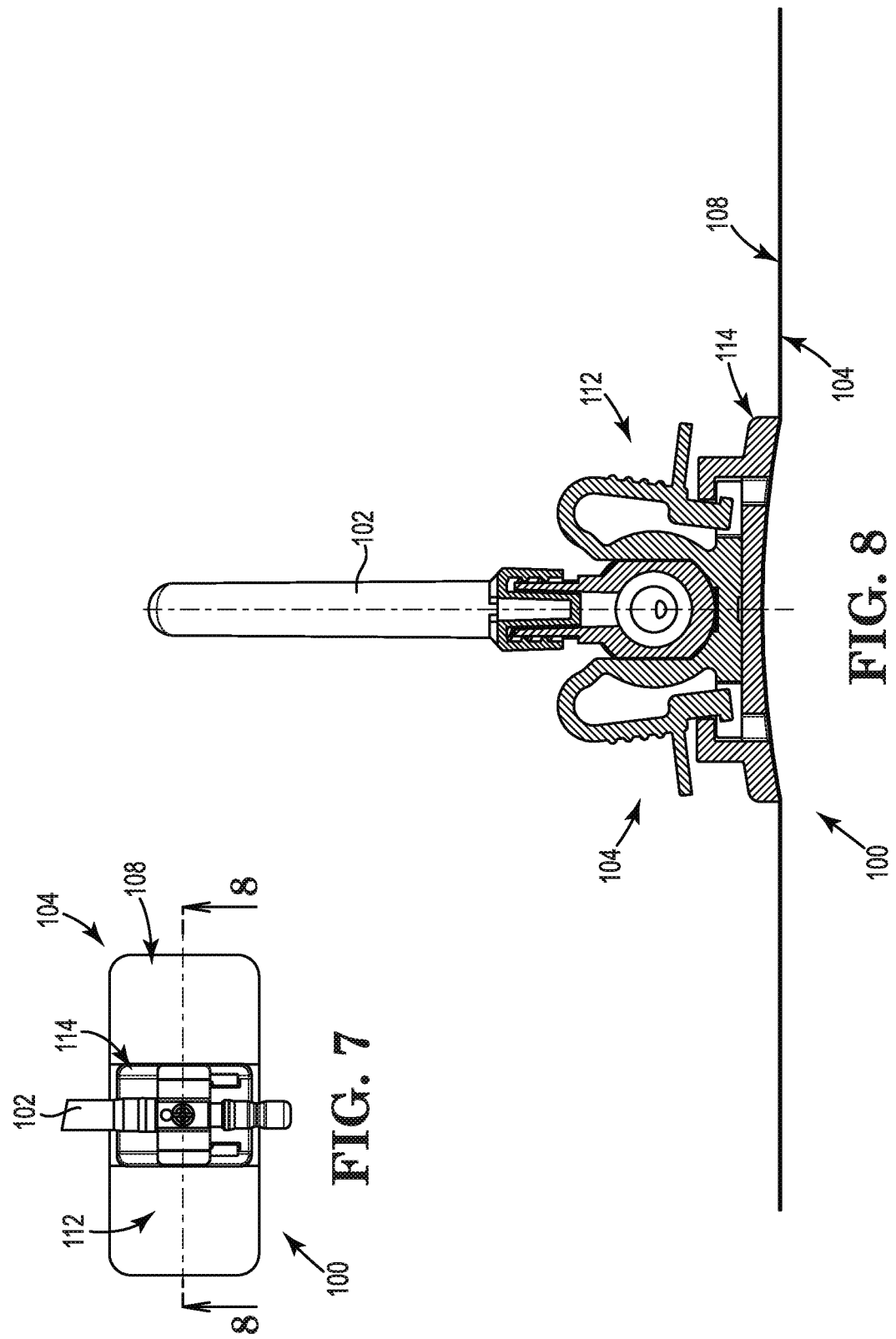

CANNULA FIXATION DEVICE

CROSS REFERENCE TO RELATED APPLICATIONS

This application is a continuation of International Application No. PCT/US2018/027176, filed Apr. 11, 2018, the disclosure of which is incorporated herein by reference.

TECHNICAL FIELD

The present disclosure relates to devices for securing a cannula in place. More specifically, the disclosure relates to devices for fixing a cannula to a subject, while allowing the cannula to slide forward and backward.

BACKGROUND

When a subject with an inserted cannula is moved, displacement of the cannula may occur, resulting in bleeding at a cannula wound site. For example, bleeding may occur at a femoral arterial cannula wound site, when a subject is moved during ECMO therapy, or CPB with femoral arterial access. This may happen for example, but not exclusively, with femoral arterial cannula e configured for bi-directional flow.

SUMMARY

Embodiments include a cannula fixation device configured to allow a cannula to be secured in place in two or more positions, including a forward position and a rearward position, selectively.

In an Example 1, a cannula fixation device comprises a base, including a platform; a subject-interface portion having an upper surface and a lower surface, the upper surface coupled to the base and the lower surface configured to be coupled to a subject; and a clip assembly configured to retain a portion of a cannula, the clip assembly being moveably coupled to the base such that the clip assembly can be selectively positioned in a first position relative to the base or a second position relative to the base.

An Example 2 includes the cannula fixation device of Example 1, wherein the clip assembly can be selectively positioned in at least a third position relative to the base.

An Example 3 includes the cannula fixation device of either of Examples 1 or 2, the base comprising a rail assembly configured to receive a rail-engagement portion of the clip assembly, wherein the rail assembly is configured such that the rail-engagement portion of the clip assembly slides between the first and second positions.

An Example 4 includes the cannula fixation device of Example 3, the rail assembly including a pair of opposite, opposed rails extending from an upper surface of the platform, each of the rails including a flange extending toward the other rail, wherein a portion of the rail-engagement portion is configured to be slideably retained between the flanges and the upper surface of the platform.

An Example 5 includes the cannula fixation device of Example 4, wherein each flange includes a first notch defined therein and configured to receive a rail-engagement locking feature when the clip assembly is in the first position, and a second notch defined therein and configured to receive the rail-engagement locking feature when the clip assembly is in the second position.

An Example 6 includes the cannula fixation device of any of Examples 1-5, wherein the clip assembly comprises a cannula-retaining portion that is configured to releasably retain the portion of the cannula.

An Example 7 includes the cannula fixation device of Example 5, the clip assembly comprising: a lower wall having a lower surface configured to be positioned adjacent to an upper surface of the base; and a pair of opposite, opposed, wing structures extending from an upper surface of the lower wall, wherein each rail-engagement locking feature is coupled to one of the wing structures, such that, when the wing structures are squeezed towards one another, the rail-engagement locking features are moved out of engagement with the corresponding notches.

An Example 8 includes the cannula fixation device of Example 7, wherein each of the wing structures includes a first section extending upward from the upper surface of the base, wherein each first section includes a curve configured to correspond to an outer surface of the portion of the cannula, and wherein the clip assembly is configured such that, when the portion of the cannula is retained in the cannula-retaining portion, and when the wing structures are squeezed towards one another, the first sections move away from one another, thereby releasing the portion of the cannula.

An Example 9 includes the cannula fixation device of Example 8, further comprising a cannula-retaining support coupled to each of the first sections of the wing structures.

An Example 10 includes the cannula fixation device of Example 9, wherein each cannula-retaining support comprises a strip of material extending from a first portion of the corresponding first section to a second portion of the corresponding first section.

An Example 11 includes the cannula fixation device of any of Examples 1-10, wherein the subject-interface portion is configured to be coupled to a subject using an adhesive and/or sutures.

An Example 12 includes a cannula fixation device, comprising: a subject-interface portion having an upper surface and a lower surface, the subject-interface portion being configured to be coupled to a subject; a base configured to be coupled to the upper surface of the subject-interface portion, the base including a platform and an upper surface; and a clip assembly configured to retain a portion of a cannula, the clip assembly being moveably coupled to the base such that the clip assembly can be selectively positioned in a first position relative to the base and a second position relative to the base, the clip assembly comprising a pair of opposite, opposed, wing structures such that, when the wing structures are squeezed toward one another, the clip assembly is able to be slid between the first position and the second position.

An Example 13 includes the cannula fixation device of Example 12, the clip assembly comprising: a lower wall having an upper surface and a lower surface, the lower surface being positioned adjacent to an upper surface of the base; and a pair of opposite, opposed, wing structures extending from the upper surface of the lower wall, each wing structure comprising a first section extending upward from the upper surface of the base, wherein the two first sections and a portion of the upper surface of the lower wall form a cannula-retaining portion of the clip assembly.

An Example 14 includes the cannula fixation device of Example 13, wherein each first section includes a curve configured to correspond to an outer surface of the portion of the cannula, and wherein the clip assembly is configured such that, when the portion of the cannula is retained in the cannula-retaining portion, and when the wing structures are pushed downwards, the first sections move away from one another, thereby releasing the portion of the cannula.

An Example 15 includes the cannula fixation device of Example 14, the base comprising a rail assembly including a pair of opposite, opposed rails extending from the upper surface of the platform, each of the rails including a flange extending toward the other rail, wherein a portion of the base is configured to be slideably retained between the flanges and the upper surface of the platform, and wherein each flange includes a first notch defined therein and configured to receive a rail-engagement locking feature when the clip assembly is in the first position, and a second notch defined therein and configured to receive the rail-engagement locking feature when the clip assembly is in the second position.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 2 is a top view of the illustrative cannula system depicted in FIG. 1, in which the clip assembly is in the most rearward position, in accordance with embodiments of the subject matter disclosed herein.

FIG. 3 is a cross sectional front view of the illustrative cannula system depicted in FIGS. 1 and 2, in which the clip assembly is in the most rearward position, in accordance with embodiments of the subject matter disclosed herein.

FIG. 5 is a top view of the illustrative cannula system, as depicted in FIG. 4, in which the clip assembly is in the most forward position, in accordance with embodiments of the subject matter disclosed herein.

FIG. 6 is a cross sectional front view of the illustrative cannula system, as depicted in FIGS. 4 and 5, in which the clip assembly is in the most forward position, in accordance with embodiments of the subject matter disclosed herein.

FIG. 7 is a top view of the illustrative cannula system depicted in FIGS. 1-6, in which the clip assembly is in an intermediate position between the most rearward position and the most forward position, in accordance with embodiments of the subject matter disclosed herein.

FIG. 8 is a cross sectional front view of the illustrative cannula system, as depicted in FIG. 7, in which the clip assembly is in an intermediate position between the most rearward position and the most forward position, in accordance with embodiments of the subject matter disclosed herein.

Figure 1:
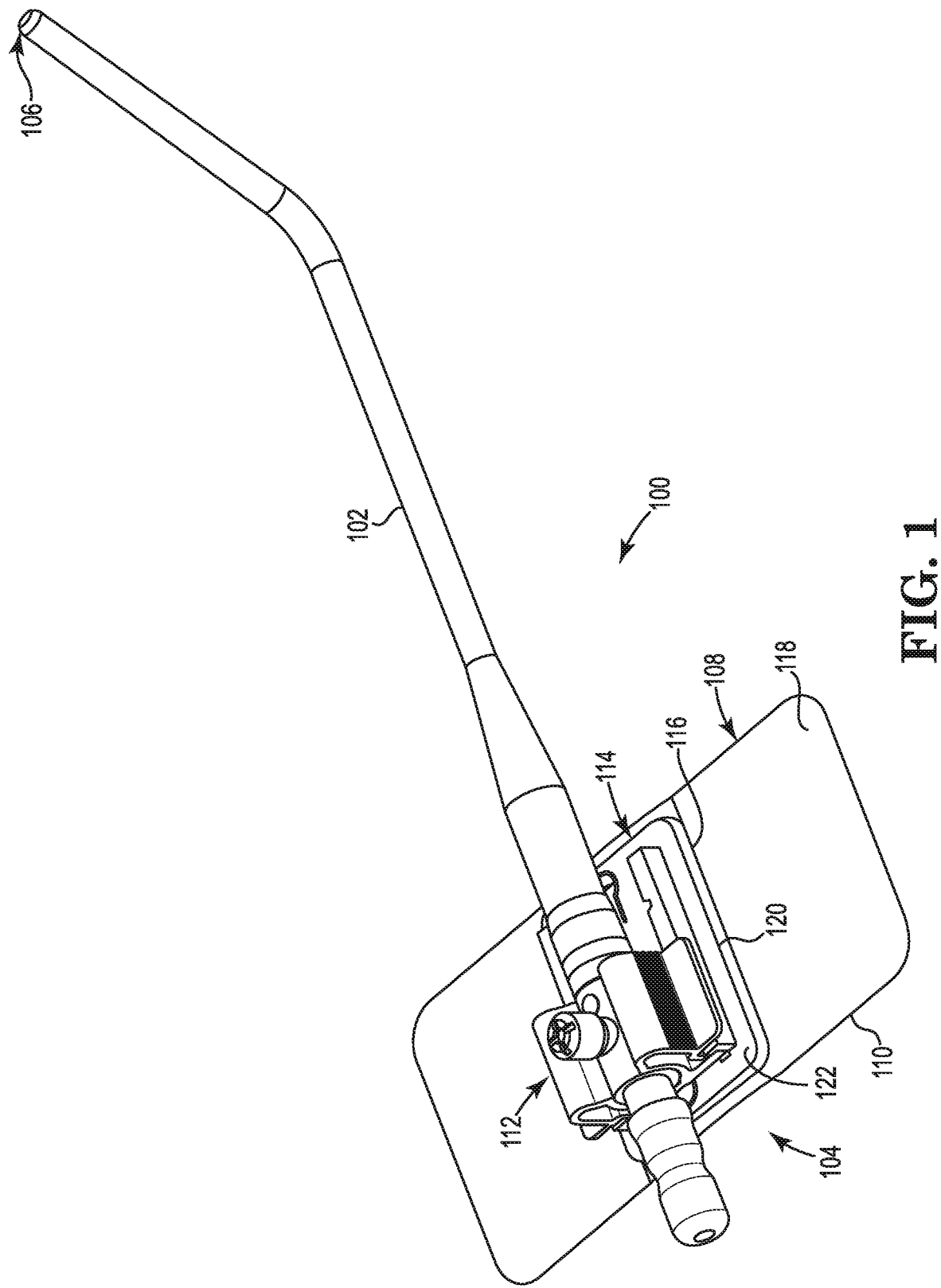
FIG. 1 is a perspective view of an illustrative cannula system, the system including a cannula retained by an illustrative cannula fixation device having a clip assembly in the most rearward position, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof. Additionally, the term "forward" is used throughout this disclosure for the sole purpose of clarity of description and is only intended to refer to a relative direction (e.g., a certain direction that is to be distinguished from another direction), and are not meant to be interpreted to mean an absolute direction, though the term may be used to refer to a direction defined in reference to a characteristic of one or more features (e.g., corresponding to the direction in which a distal end—the end that is inserted into a subject—of a cannula is located, as compared to a proximal end of the cannula). Similarly, the term "rearward" is used throughout this disclosure for the sole purpose of clarity of description and is only intended to refer to a relative direction that is at least approximately opposite a direction referred to by the term "forward," though the term may be used to refer to a direction defined in reference to a characteristic of one or more features (e.g., corresponding to the direction in which a proximal end of a cannula is located, as compared to a distal end of the cannula).

DETAILED DESCRIPTION

Embodiments include a cannula fixation device configured to facilitate moving a cannula between two or more positions, such as, for example, a first position (e.g., a most rearward position), a second position (e.g., a most forward position), and/or one or more intermediate positions between the most rearward position and the most forward position. The cannula fixation device may include a base configured to be affixed to a subject's skin near a cannula wound site (e.g., using an adhesive, sutures, a strap, a wrap, a sleeve, a garment, etc.). The base may be moveably coupled to a cannula securing assembly such that the cannula securing assembly may be securely positioned in varying degrees closer to the cannula wound site or further from the cannula wound site. The cannula securing assembly may be movably coupled to the base via a slide, rail, groove, track, threads, hinge, arm, any combination thereof, and/or any other known mechanism for moveably coupling the cannula securing assembly to the base. The cannula securing assembly may be secured in position with respect to the base using a groove, clip, snap, strap, screw, post, clamp, velcro, friction fit, pressure fit, latch, tie, any combination thereof, and any other known mechanism that could be used to secure the cannula securing assembly in position with respect to the base.

The cannula securing assembly may be configured to receive and secure the cannula such that the cannula in combination with the cannula securing assembly are moveably coupled to the base. When the cannula securing assembly is positioned closer to the cannula wound site, the cannula is inserted further into the subject and, when the cannula securing assembly is positioned further from the wound site, the cannula is drawn further out of the wound site. The cannula securing assembly may secure the cannula using a groove, clip, strap, clamp, velcro, friction fit, pressure fit, latch, tie, any combination thereof, and/or any other known mechanism that could be used to secure the cannula to the cannula securing assembly.

In embodiments, the cannula securing assembly may be a clip assembly and the cannula may be press fit, tie wrapped (e.g., by means of a clip), and/or otherwise secured to a clip assembly. The clip assembly may be horizontally slidable along a rail assembly of a base (or platform) or otherwise moveable between two or more positions with respect to the base to provide different depths of cannula insertion at the wound site when the cannula is secured to the cannula fixation device. The base may be coupled to a subject-interface portion for securing the base to the subject. The subject-interface portion may include an adhesive pad and/or a structure (e.g., pad with suturing holes) configured to be sutured to the subject's skin. The clip assembly may be configured to prevent any axial rotation of the cannula and to allow rearward and forward movements of the cannula, such as, for example, between two or more positions.

FIGS. 1-3 depict various views of a cannula system 100, the system including a cannula 102 retained by an illustrative cannula fixation device 104. In embodiments, the cannula fixation device 104 may be configured to secure the cannula 102 in place, while a distal end 106 of the cannula 102 is inserted into a subject. As shown, the cannula fixation device 104 may include a subject-interface portion 108 configured to be coupled to a subject's skin. In embodiments, the subject-interface portion 108 may include an adhesive portion 110 (e.g., an adhesive lower surface of the subject-interface portion). According to embodiments, the subject-interface portion 108 may additionally or alternatively include holes, be of a suitable material, and/or otherwise be configured to permit suturing of the cannula fixation device 104 to the subject's skin (as shown, e.g., in FIG. 14).

Figure 4:
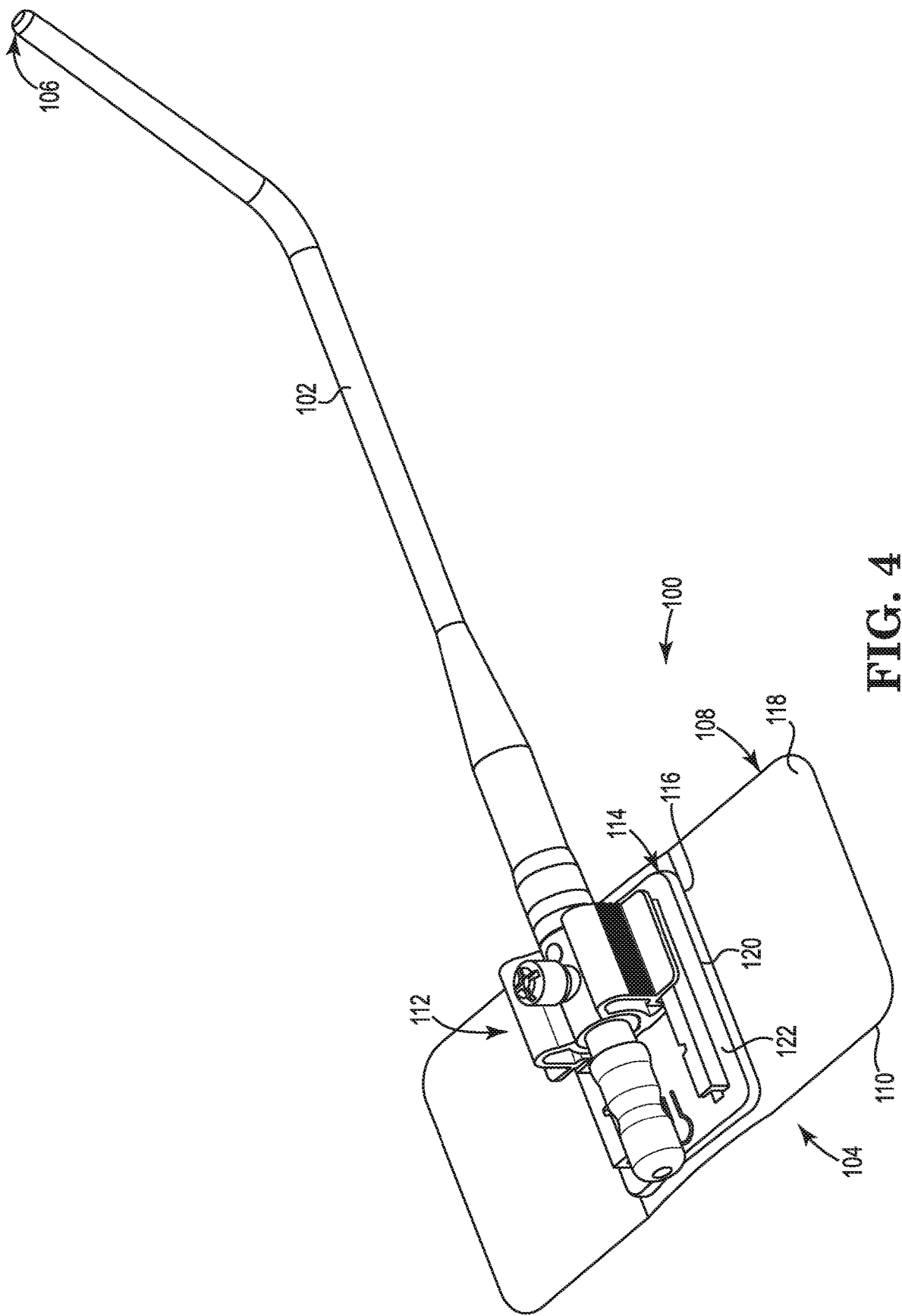
FIG. 4 is a perspective view of the illustrative cannula system depicted in FIGS. 1-3, in which the clip assembly is in the most forward position, in accordance with embodiments of the subject matter disclosed herein.
Figure 14:
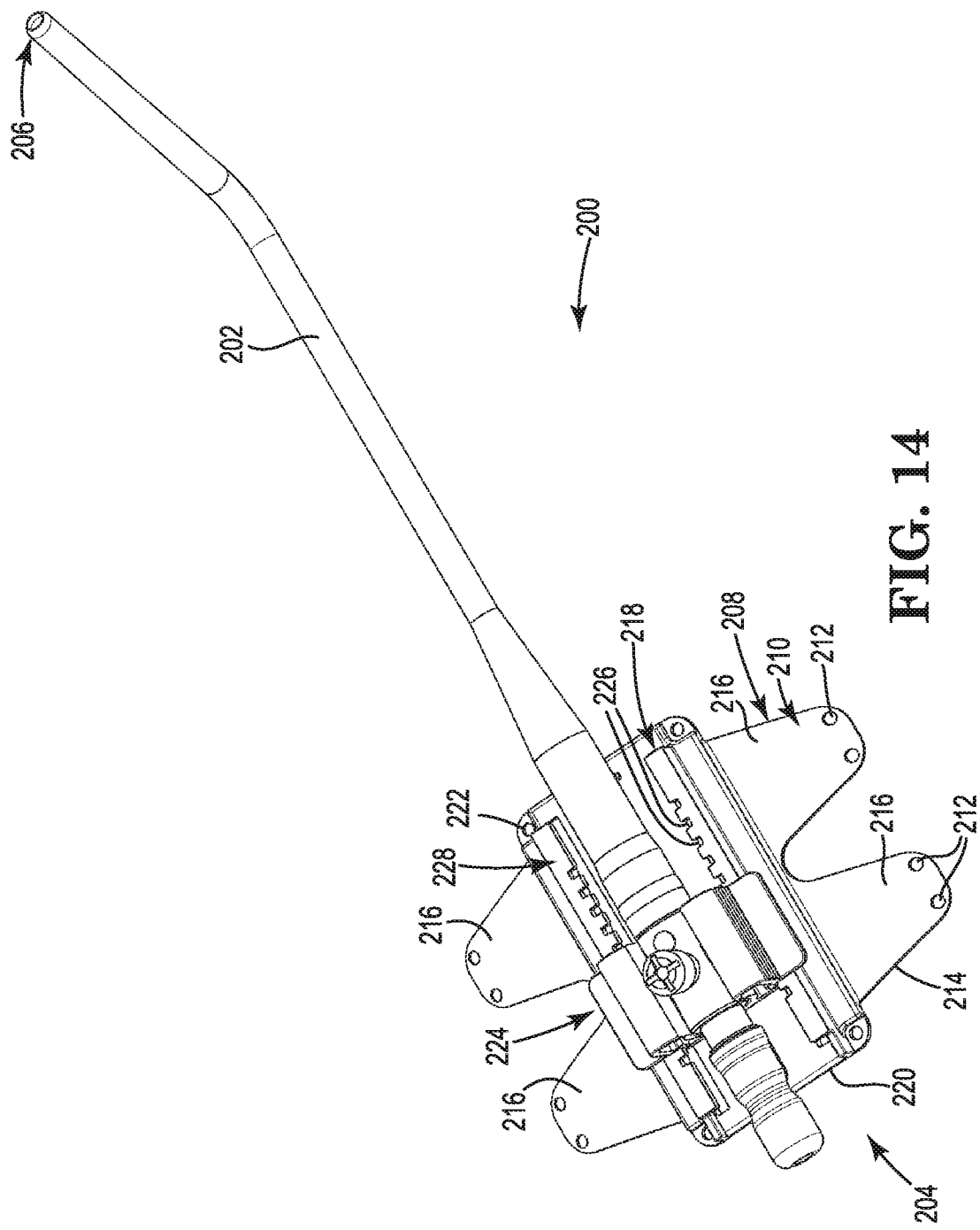
FIG. 14 is a perspective view of another illustrative cannula system, the system including a cannula retained by another illustrative cannula fixation device, in which multiple positions for the clip assembly are provided, and including a base with lateral wings for fixing the cannula fixation device to the skin of the subject, either by an adhesive pad or by sutures (through the holes provided therein).

The cannula fixation device 104 may further include a clip assembly 112 moveably coupled to a base 114. As shown, the base 114 may be configured to be coupled, via a lower surface 116 thereof, to an upper surface 118 of the subject-interface portion 108. According to embodiments, the clip assembly 112 is configured to be positioned in at least two different positions relative to the base 114. For example, as shown in FIGS. 1-3, the clip assembly 112 may be positioned in a first position relative to the base 114, where the first position is the most rearward position—that is, for example, a position that is farthest away from a cannula wound site and/or distal end 106 of the cannula 102 (when the cannula is inserted into the subject). As shown in FIGS. 4-6, the clip assembly 112 may be positioned in a second position relative to the base 114, where the second position is the most forward position—that is, for example, a position that is closest to the cannula wound site and/or the distal end 106 of the cannula 102 (when the cannula is inserted into the subject). According to embodiments, and as shown in FIGS. 7 and 8, the clip assembly 112 may be placed into an intermediate position between the first and second positions. In embodiments, the clip assembly may be placed into any number of positions. Although the intermediate position depicted in FIGS. 7 and 8 is an unlocked position (that is, a position in which the clip assembly 112 is not prevented from moving relative to the base 114 such as, for example, a position of the clip assembly 112 during movement of the clip assembly 112 from a first position to a second position), any number of intermediate positions may include locked positions (e.g., as depicted in FIG. 14).

A cannula fixation device 104 configured in accordance with embodiments of the subject matter disclosed herein may be used, for example, to hold a cannula 102 in place against a subject's skin and inserted into the cannula wound site as a subject is moving or being moved so that the cannula does not dislodge to an extent that would cause bleeding (e.g., past a bi-directional flow port at the elbow of a bi-directional flow cannula). In this manner, embodiments of the cannula fixation device 104 described herein may reduce the chance of bleeding at the cannula wound site, which might otherwise occur if displacement of the cannula sufficiently retracts the cannula from the wound site. For example, a cannula 102 may be pushed (and firmly secured in place) further into a femoral artery, by positioning it, by repositioning the clip assembly 112, into a forward position (e.g., any one of any number of different positions that are forward with respect to a previous position). This may facilitate reducing of bleeding when using cannulae that have elbows such as, for example, the cannulae described in U.S. Pat. No. 8,795,253, assigned to Sorin Group Italia, S.R.L., of Milano, Italy, an embodiment of which is depicted as cannula 102 herein. In this way, for example, an elbow of the cannula (where the bi-directional flow port is located) may be temporarily advanced into the femoral artery, thus minimizing the risk of bleeding at the wound site. After the subject is rotated, or moved, the bi-directional cannula may be retracted to its original backward position and secured in place so that its normal operation is resumed.

FIGS. 9-12 include various views of the illustrative cannula fixation device 104, in accordance with embodiments of the subject matter disclosed herein. According to embodiments, as shown, the base 114 includes a platform 120 having the lower surface 116 and an opposite, upper surface 122. The base 114 includes a rail assembly 124 disposed on the platform 120. As shown, for example, the rail assembly 124 may include a pair of opposite, opposed rails 124A, 124B extending from the upper surface 122 of the platform 120. The rail 124A includes a wall 126A extending away from the upper surface 122 of the platform 120 and, in embodiments, being oriented at least approximately orthogonal to the upper surface 122 of the platform 120. A flange 128A extends away from an upper edge 130A of the wall 126A. In embodiments, the flange 128A may be oriented at least approximately orthogonal to the wall 126A, and may extend toward the other rail 124B, e.g., to form an "L"-shaped rail 124A. As shown, the flange 128A may include a number of notches (or slots) 132A defined therein and configured to receive a locking feature 134A of the clip assembly 112.

Similarly, rail 124B includes a wall 126B extending away from the upper surface 122 of the platform 120 and, in embodiments, being oriented at least approximately orthogonal to the upper surface 122 of the platform 120. A flange 128B extends away from an upper edge 130B of the wall 126B. In embodiments, the flange 128B may be oriented at least approximately orthogonal to the wall 126B, and may extend toward the other rail 124A, e.g., to form an "L"-shaped rail 124B. As shown, the flange 128B may include a number of notches 132B defined therein and configured to receive a locking feature 134B of the clip assembly 112.

According to embodiments, the clip assembly 112 (and, correspondingly, the rail assembly 124) may be designed in any number of different ways so as to facilitate being able to move the clip assembly 112 between at least two positions relative to the base 114, as shown, for example, in FIGS. 1-6. In embodiments, as shown in FIGS. 9-11, the clip assembly 112 includes a cannula-retaining portion 136 that is configured to releasably retain a portion of a cannula 102, and a rail-engagement portion 138 that is configured to moveably (e.g., slideably) couple the clip assembly 112 to the base 114.

The cannula retaining portion 136 may include any number of cannula-retaining mechanisms such as, for example, clips, straps, interference-fit receiving structures, and/or the like.

Figure 9:
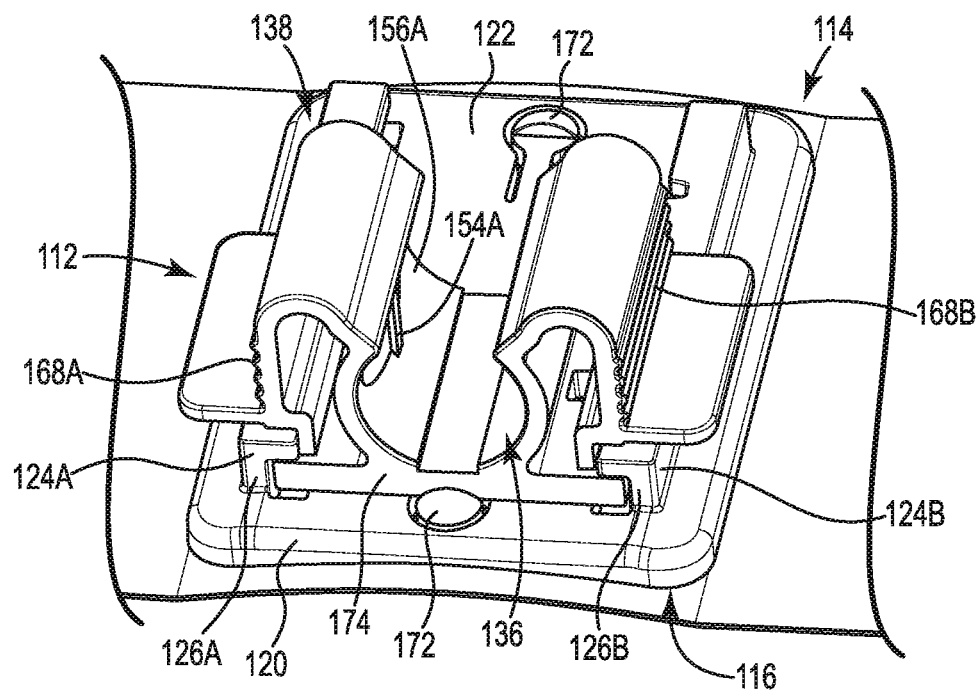
FIG. 9 is a front perspective view of the illustrative cannula fixation device depicted in FIGS. 1-8, in which the clip assembly is in the most rearward position, in accordance with embodiments of the subject matter disclosed herein.
Figure 10:
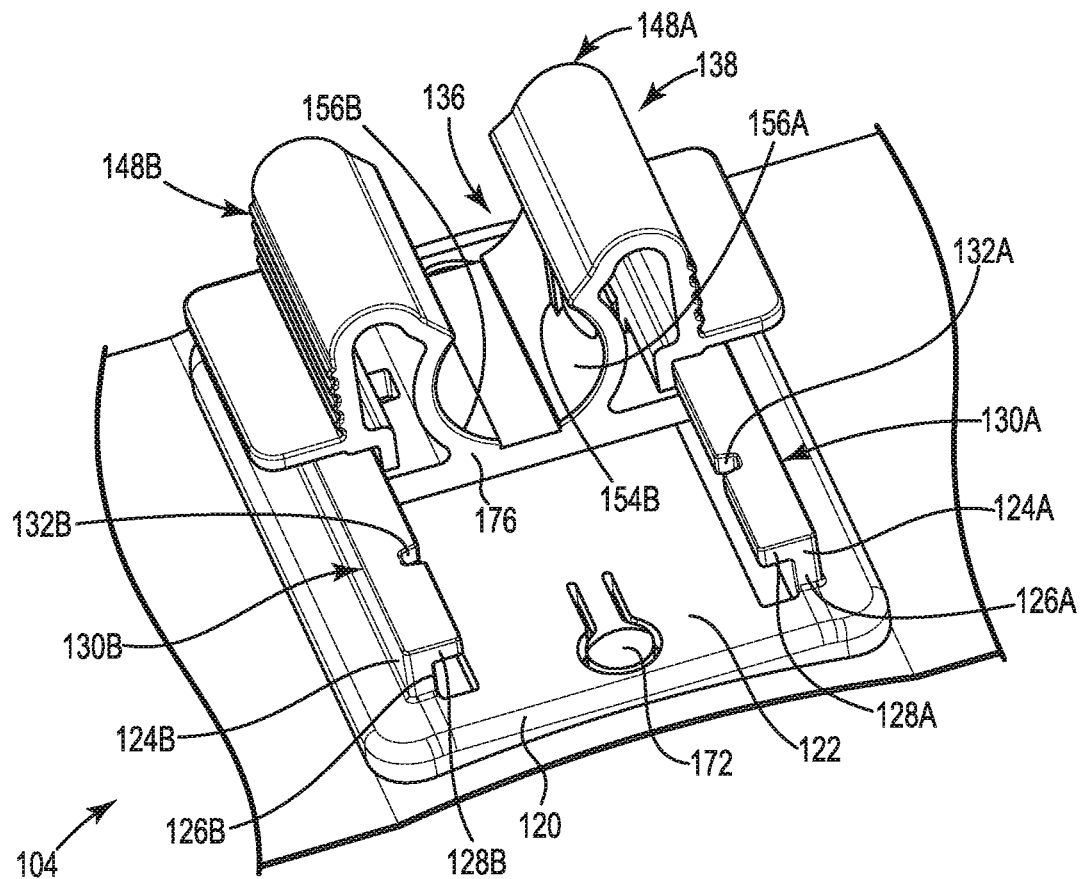
FIG. 10 is a back perspective view of the illustrative cannula fixation device, as depicted in FIG. 9, in which the clip assembly is in the most rearward position, in accordance with embodiments of the subject matter disclosed herein.
Figure 11:
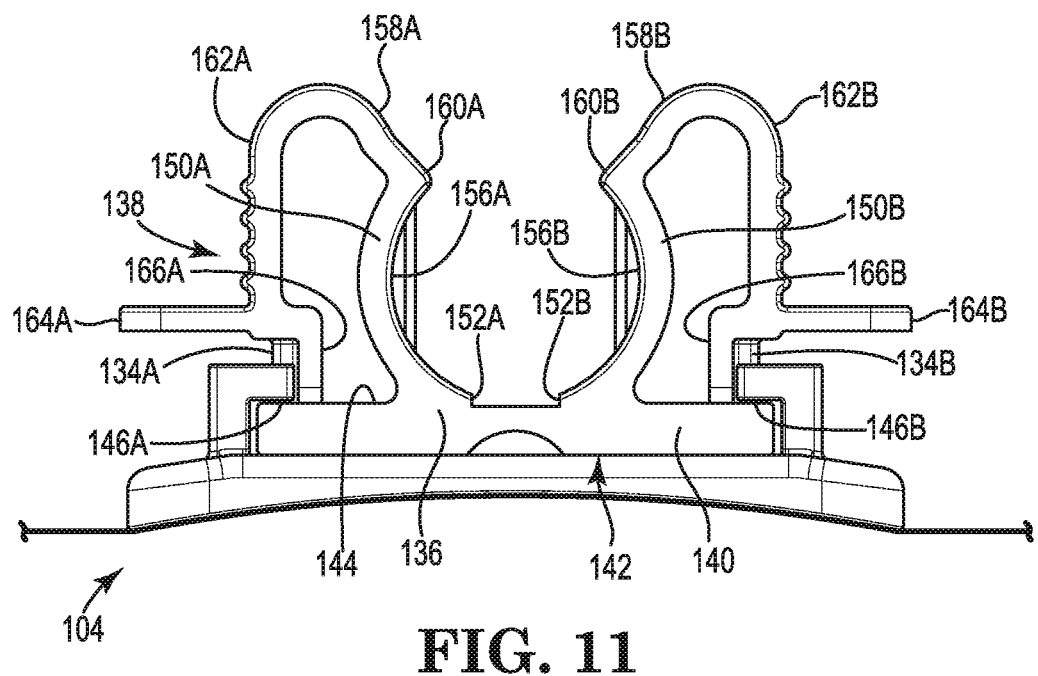
FIG. 11 is a front view of the illustrative cannula fixation device, as depicted in FIGS. 9 and 10, in which the clip assembly is in the most rearward position, in accordance with embodiments of the subject matter disclosed herein.
Figure 12:
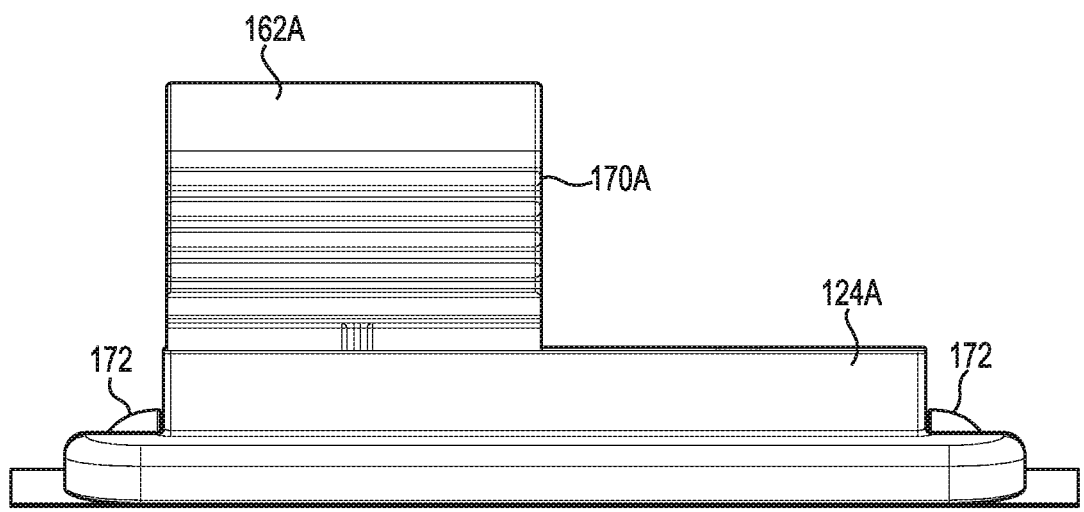
FIG. 12 is a side view of the illustrative cannula fixation device, as depicted in FIGS. 9-11, in which the clip assembly is in the most rearward position, in accordance with embodiments of the subject matter disclosed herein.

According to embodiments, the clip assembly 112 may be configured such that the cannula-retaining portion 136 and the rail-engagement portion 138 are integrated, as shown, for example, in FIGS. 9-11. In the illustrative device 104, the rail-engagement portion 138 may include at least a portion of a lower wall 140 configured so that a lower surface 142 thereof engages, or is otherwise positioned adjacent to, the upper surface 122 of the platform 120. At least a portion of an opposite, upper surface 144 may be configured to be positioned below the flanges 128A and 128B. In this manner, in embodiments, a lower surface 146A and 146B of the flanges 128A and 128B, respectively, may be configured to engage portions of the upper surface 144 of the lower wall 140 of the clip assembly 112.

As shown, a pair of opposite, opposed, wing structures 148A and 148B extend from the upper surface 144 of the lower wall 140. The wing structure 148A may include, for example a first section 150A coupled, at a first end 152A, to the upper surface 144 of the lower wall 140 and extending upward, in a curve, from the upper surface 144. Similarly, the wing structure 148B may include, for example a first section 150B coupled, at a first end 152B, to the upper surface 144 of the lower wall 140 and extending upward, in a curve that is at least approximately the mirror image of the curve of the first section of the wing structure 148A, from the upper surface 144. In embodiments, the first section of 150A, the first section of 150B, and a portion of the upper surface 144 disposed between the two first sections of 150A and of 150B form the cannula-retaining portion 136 of the clip assembly 112. In embodiments, one or more of the wing structures 148A and 148B may include a flange (not shown) extending toward an adjacent rail 124A and/or 124B, where the flange is configured to be slideably engaged between the lower surface 146A and/or 146B of the flange 128A and/or 128B and the upper surface 144 of the lower wall 140 of the clip assembly 112 and/or a portion of the upper surface 122 of the platform 120.

In embodiments, the clip assembly 112 is formed from a semi-flexible plastic, polymer, or similar material, such that each wing structure 148A and 148B is configured to return, upon being displaced, to an original position, where the original position is configured such that the two first sections form retain the cannula 102 in a manner such that, in order to remove the cannula 102, at least one of the two wing structures 148A and 148B must be actuated such that the respective first section 150A and/or 150B, is moved away from the cannula 102. For example, the curves of the first sections of 150A and of 150B may be configured to correspond to a curvature of an outer surface of the cannula 102.

The cannula-retaining portion 136 may also include, in embodiments, cannula-retaining support surfaces 154A and 154B coupled to each of the two first sections 150A and 150B, respectively. According to embodiments, an inner surface 156A and 156B of one or more of the first and second sections 150A and 150B, respectively, may include any number of different features configured to facilitate retaining the cannula 102 within the cannula-retaining portion 136. For example, the surfaces 156A and 156B may include rough texturing, raised features, rubber, and/or the like.

As is further shown, the wing structure 148A may further include a second section 158A that extends away from an upper edge 160A of the first section 150A and curves toward the platform 120. A third section 162A extends downward from the second section 158A; a shelf 164A extending away from the third section 162A; and an "L"-shaped engagement section 166A extending inward from the shelf 164A. The engagement section 166A may include one or more tabs (and/or or other locking feature) 134A extending outward (e.g., away from the cannula-retaining portion 136) and configured to fit within the slots 132A to lock the clip assembly 112 in one of the multiple positions corresponding to the slots 132A Similarly, the wing structure 148B may further include a second section 158B that extends away from an upper edge 160B of the first section 150B and curves toward the platform 120. A third section 162B extends downward from the second section 158B; a shelf 164B extending away from the third section 162B; and an "L"-shaped engagement section 166B extending inward from the shelf 164B. The engagement section 166B may include one or more tabs 134B extending outward (e.g., away from the cannula-retaining portion 136) and configured to fit within the slots 132B to lock the clip assembly 112 in one of the multiple positions corresponding to the slots 132B.

The clip assembly 112 may be configured such that, for example, when a user squeezes on the outside surfaces 168A and 168B of the third sections 162A and 162B, respectively, the engagement sections 166A and 166B move away from the corresponding rails 124A and 124B, thereby moving the tabs 134A and 134B out of the notches 132A and 132B so that the clip assembly can be slid forward or backward to a different position, as shown, for example, in FIG. 8. In embodiments, as shown, the outside surfaces 168A and 168B of the third sections 162A and 162B, respectively, may include one or more grip features 170A and 170B, respectively, configured to facilitate a user maintaining a grip on the clip assembly. That is, for example, in embodiments, the grip features 170A and 170B may include horizontal rib features (as shown), rough texture, other raised features, and/or the like. According to embodiments, the third sections 162A and/or 162B may include any number of other features configured to facilitate gripping such as, for example, indentions, grooves, and/or the like.

Figure 13:
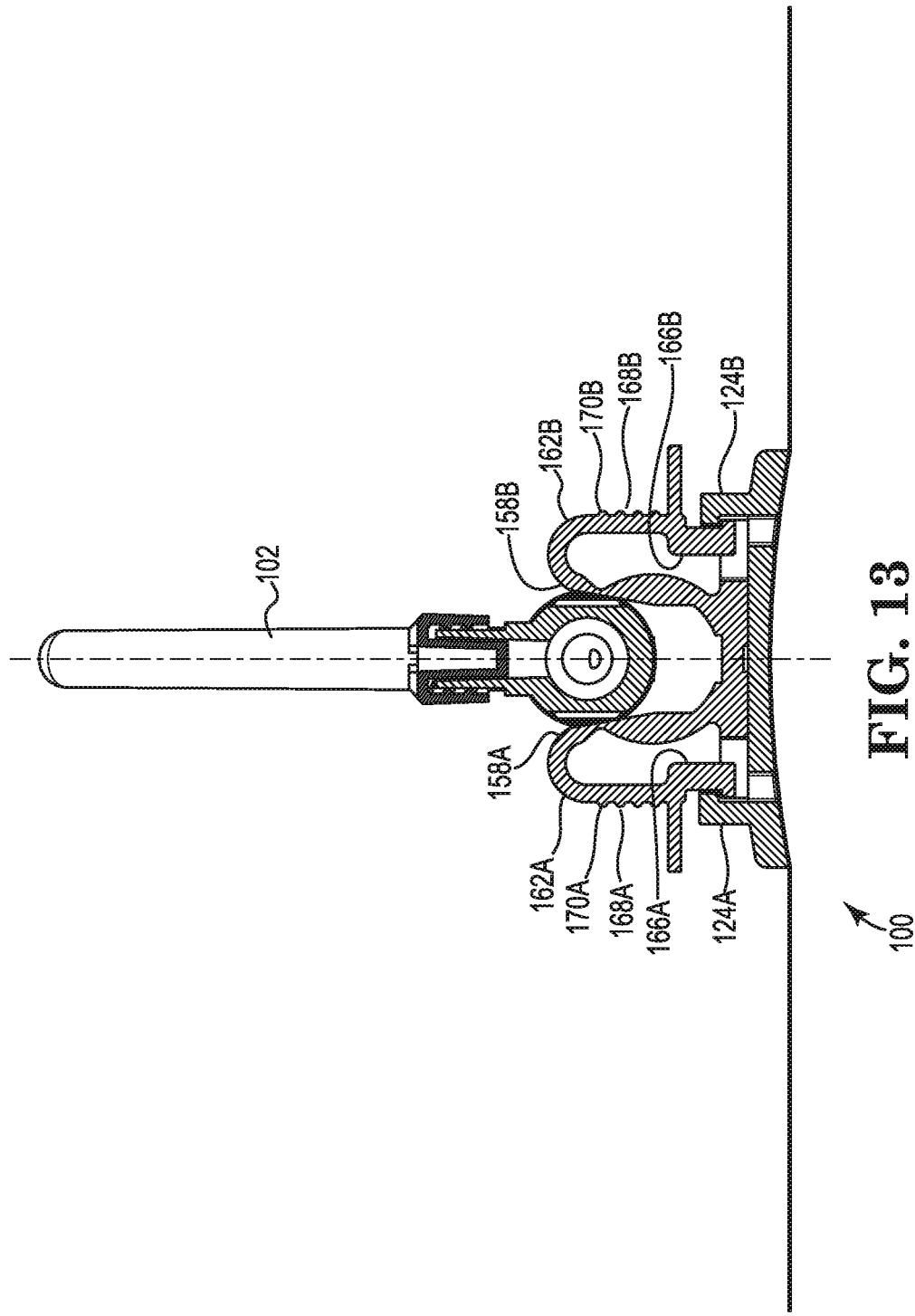
FIG. 13 is a cross sectional front view of the illustrative cannula fixation device depicted in FIGS. 1-12, in which the clip assembly is in the most rearward position, showing insertion of the cannula to a cannula-retaining portion of the clip assembly, in accordance with embodiments of the subject matter disclosed herein.

Additionally, or alternatively, the clip assembly 112 may be configured such that, when a user squeezes on the outside surfaces 168A and 168B of the third sections 162A and 162B, respectively, the first sections 150A and 150B move away from the cannula 102 (or the space in which the cannula 102 is configured to be retained) to facilitate releasing the cannula 102 or retaining the cannula 102. In embodiments, the clip assembly 112 may be configured such that the cannula 102 can be placed within the cannula-retaining portion 136 by pushing the cannula 102 down against the second sections 158A and 158B, as shown in FIG. 13, which causes the first sections 150A and 150B to move outward, allowing the cannula 102 to be positioned between the first sections 150A and 150B which, when the assembly is released by the user, move back toward the cannula 102, thereby causing retention of the cannula 102 within the cannula-retaining portion 136.

The illustrative cannula fixation device 104 shown in FIGS. 1-13 is not intended to suggest any limitation as to the scope of use or functionality of embodiments of the present disclosure. The illustrative cannula fixation device 104 should not be interpreted as having any dependency or requirement related to any single component or combination of components illustrated therein. Additionally, various components depicted in FIGS. 1-13 may be, in embodiments, integrated with various ones of the other components depicted therein (and/or components not illustrated), all of which are considered to be within the ambit of the subject matter disclosed herein.

FIG. 14 is a perspective view of another cannula system 200, in accordance with embodiments of the subject matter disclosed herein. As shown, the cannula system 200 includes a cannula 202 retained by an illustrative cannula fixation device 204. In embodiments, and similar to the cannula fixation device 104 depicted in FIGS. 1-13, the cannula fixation device 204 may be configured to secure the cannula 202 in place, while a distal end 206 of the cannula 202 is inserted into a subject. The cannula fixation device 204 may include a subject-interface portion 208 configured to be coupled to a subject's skin. As shown, the subject-interface portion 208 may include a suturable portion 210 that may include, for example, one or more holes 212 for receiving one or more portions of a suture configured to suture the suturable portion 210 to the subject's skin. Additionally or alternatively, the suturable portion 210 may be constructed from a material suitable for receiving sutures therethrough. In embodiments, any number of other features may be used to facilitate suturing the suturable portion 210 to a subject's skin. In embodiments, the subject-interface portion 208 and/or the suturable portion 210 may also include an adhesive lower surface 214.

As shown in FIG. 14, the subject-interface portion 208 and/or the suturable portion 210 may include a number of flaps 216 configured to be sutured and/or adhered to the subject's skin. Embodiments of the cannula fixation device 204 may include any number of flaps 216 (e.g., 1, 2, 3, 4, 5, 6, etc.). As shown, the subject-interface portion 208 and/or the suturable portion 210 are coupled to a base 218. The subject-interface portion 208 and/or the suturable portion 210 may be coupled to a lower surface 220 of the base 218. Additionally or alternatively, the subject-interface portion 208 and/or the suturable portion 210 may extend from one or more sides of the base 218. In embodiments, the subject-interface portion 208 and/or the suturable portion 210 may be formed from a single piece of one or more materials, or may be formed from multiple pieces of one or more materials. In embodiments, as shown, the base 218 may include one or more suture holes 222 disposed therein and configured for receiving one or more sutures. The suture holes 222 in the base 218 may be provided in addition to, or in lieu of, the suture holes 212 in the suturable portion 210 of the subject-interface portion 208.

As is further shown in FIG. 14, the cannula fixation device 204 may further include a clip assembly 224 moveably coupled to the base 218. According to embodiments, the clip assembly 224 is configured to be positioned in at least two different positions relative to the base 218. For example, the clip assembly 224 may be positioned in a first position relative to the base 218, where the first position is the most rearward position—that is, for example, a position that is farthest away from a cannula wound site and/or distal end 206 of the cannula 202 (when the cannula is inserted into the subject). Additionally, the clip assembly 224 may be positioned in a second position relative to the base 218, where the second position is the most forward position—that is, for example, a position that is closest to the cannula wound site and/or the distal end 206 of the cannula 202 (when the cannula is inserted into the subject). According to embodiments, and as shown in FIG. 14, the clip assembly 224 may be placed into any one of a number of intermediate positions between the first and second positions.

In contrast to the intermediate position depicted in FIGS. 7 and 8, which is an unlocked position (that is, a position in which the clip assembly 112 is not prevented from moving relative to the base 114 such as, for example, a position of the clip assembly 112 during movement of the clip assembly 112 from a first position to a second position), the intermediate positions depicted in FIG. 14 include locked positions. The locked intermediate positions depicted in FIG. 14 are facilitated by intermediately-disposed slots 226 disposed in one or more rails of a rail assembly 228 that may be selectively engaged by one or more corresponding locking features (not shown) of the clip assembly. According to embodiments, the rail assembly 228 may be similar to the rail assembly 124 depicted in FIGS. 9-12. Similarly, any number of other features depicted in FIGS. 1-13 may be identical to, or similar to, corresponding features depicted in FIG. 14. That is, for example, any number of the features depicted in FIG. 14.

The illustrative cannula fixation device 204 shown in FIG. 14 is not intended to suggest any limitation as to the scope of use or functionality of embodiments of the present disclosure. The illustrative cannula fixation device 204 should not be interpreted as having any dependency or requirement related to any single component or combination of components illustrated therein. Additionally, various components depicted in FIG. 14 may be, in embodiments, integrated with various ones of the other components depicted therein (and/or components not illustrated), all of which are considered to be within the ambit of the subject matter disclosed herein.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. For example, in embodiments (as shown in FIGS. 9-10), the base 114 may include one or more stop features 172 extending from the upper surface 122 of the platform 120 and configured to engage a front or back surface 174 or 176 of the clip assembly 112 to limit the distance that the clip assembly 112 can slide. Accordingly, the scope of the present disclosure is intended to embrace all such alternatives, modifications, and variations as fall within the scope of the claims, together with all equivalents thereof.

What is claimed is:

1. A cannula fixation device, comprising:
    a base, including a platform and having a first end and an opposite second end;
    a subject-interface portion having an upper surface and a lower surface, the upper surface coupled to the base and the lower surface configured to be coupled to a subject; and
    a clip assembly configured to retain a portion of a cannula, the clip assembly including a first end and an opposite second end, the clip assembly being moveably coupled to the base such that the clip assembly can be selectively positioned in a forwardmost position relative to the base in which the first end of the clip assembly is moved toward the first end of the base or a rearwardmost position relative to the base in which the second end of the clip assembly is moved toward the second end of the base,
    wherein the first and second ends of the clip assembly are positioned between the first and second ends of the base when the clip assembly is in the forwardmost position, and
    wherein the first and second ends of the clip assembly are positioned between the first and second ends of the base when the clip assembly is in the rearwardmost position;
    wherein the clip assembly is configured to receive the portion of a cannula through an opening in an upper surface of the clip assembly and retain the cannula therein while the opening in the upper surface of the clip assembly remains open after receiving the portion of the cannula.

2. The cannula fixation device of claim 1, wherein the clip assembly can be selectively positioned in at least a third position relative to the base, the third position being between the forwardmost position and the rearwardmost position.

3. The cannula fixation device of claim 1, the base comprising a rail assembly configured to receive a rail-engagement portion of the clip assembly, wherein the rail assembly is configured such that the rail-engagement portion of the clip assembly slides between the forwardmost position and the rearwardmost position.

4. The cannula fixation device of claim 3, the rail assembly including a pair of opposite, opposed rails extending from an upper surface of the platform, each of the rails including a flange extending toward the other rail, wherein a portion of the rail-engagement portion is configured to be slideably retained between the flanges and the upper surface of the platform.

5. The cannula fixation device of claim 4, wherein each flange includes a first notch defined therein and configured to receive a rail-engagement locking feature when the clip assembly is in the forwardmost position, and a second notch defined therein and configured to receive the rail-engagement locking feature when the clip assembly is in the rearwardmost position.

6. The cannula fixation device of claim 1, wherein the clip assembly comprises a cannula-retaining portion that is configured to releasably retain the portion of the cannula.

7. The cannula fixation device of claim 5, the clip assembly comprising:
    a lower wall having a lower surface configured to be positioned adjacent to an upper surface of the base; and
    a pair of opposite, opposed, wing structures extending from an upper surface of the lower wall, wherein each rail-engagement locking feature is coupled to one of the wing structures, such that, when the wing structures are squeezed towards one another, the rail-engagement locking features are moved out of engagement with the corresponding notches.

8. The cannula fixation device of claim 7, wherein each of the wing structures includes a first section extending upward from the upper surface of the base, wherein each first section includes a curve configured to correspond to an outer surface of the portion of the cannula, and wherein the clip assembly is configured such that, when the portion of the cannula is retained in a cannula-retaining portion, and when the wing structures are squeezed towards one another, the first sections move away from one another, thereby releasing the portion of the cannula.

9. The cannula fixation device of claim 8, further comprising a cannula-retaining support coupled to each of the first sections of the wing structures.

10. The cannula fixation device of claim 9, wherein each cannula-retaining support comprises a strip of material extending from a first portion of the corresponding first section to a second portion of the corresponding first section.

11. The cannula fixation device of claim 1, wherein the subject-interface portion is configured to be coupled to a subject using an adhesive and/or sutures.

12. A cannula fixation device, comprising:
a subject-interface portion having an upper surface and a lower surface, the subject-interface portion being configured to be coupled to a subject;
a base configured to be coupled to the upper surface of the subject-interface portion, the base including a platform and an upper surface, the base including a first end and an opposite second end; and
a clip assembly configured to retain a portion of a cannula through an opening in an upper surface of the clip assembly, the clip assembly being moveably coupled to the base along an axis, the axis extending from the first end of the base to the second end of the base such that the clip assembly can be selectively positioned in a first position relative to the base and a second position relative to the base, the clip assembly comprising a pair of opposite, opposed, wing structures such that, when the wing structures are squeezed toward one another, the clip assembly is able to be slid between the first position and the second position;
wherein the clip assembly includes a first end and an opposite second end, the clip assembly extending along the axis, wherein both the first end of the clip assembly and the second end of the clip assembly are positioned between the first end of the base and the second end of the base in the first position;
wherein the clip assembly is configured to receive the portion of a cannula through an opening in an upper surface of the clip assembly and retain the cannula therein while the opening in the upper surface of the clip assembly remains open after receiving the portion of the cannula.

13. The cannula fixation device of claim 12, the clip assembly comprising: a lower wall having an upper surface and a lower surface, the lower surface being positioned adjacent to an upper surface of the base; and the pair of opposite, opposed, wing structures extending from the upper surface of the lower wall, each wing structure comprising a first section extending upward from the upper surface of the base, wherein the two first sections and a portion of the upper surface of the lower wall form a cannula-retaining portion of the clip assembly.

14. The cannula fixation device of claim 13, wherein each first section includes a curve configured to correspond to an outer surface of the portion of the cannula, and wherein the clip assembly is configured such that, when the portion of the cannula is retained in the cannula-retaining portion, and when the wing structures are pushed downwards, the first sections move away from one another, thereby releasing the portion of the cannula.

15. The cannula fixation device of claim 14, the base comprising a rail assembly including a pair of opposite, opposed rails extending from the upper surface of the platform, each of the rails including a flange extending toward the other rail, wherein a portion of the base is configured to be slideably retained between the flanges and the upper surface of the platform, and wherein each flange includes a first notch defined therein and configured to receive a rail-engagement locking feature when the clip assembly is in the first position, and a second notch defined therein and configured to receive the rail-engagement locking feature when the clip assembly is in the second position.

16. The cannula fixation device of claim 12, wherein both the first end of the clip assembly and the second end of the clip assembly are positioned between the first end of the base and the second end of the base in the second position.

17. A cannula fixation device, comprising:
a subject-interface portion having an upper surface and a lower surface, the subject-interface portion being configured to be coupled to a subject;
a base configured to be coupled to the upper surface of the subject-interface portion, the base including a platform and an upper surface; and
a clip assembly configured to retain a portion of a cannula through an opening in an upper surface of the clip assembly, the clip assembly being moveably coupled to the base such that the clip assembly can be selectively positioned in a first position relative to the base and a second position relative to the base, the clip assembly comprising a pair of opposite, opposed, wing structures such that, when the wing structures are squeezed toward one another, the clip assembly is able to be slid between the first position and the second position;
the clip assembly including:
a lower wall having an upper surface and a lower surface, the lower surface being positioned adjacent to an upper surface of the base; and
the pair of opposite, opposed, wing structures extending from the upper surface of the lower wall, each wing structure of the pair of opposite, opposed wing structures comprising a first section extending upward from the upper surface of the base, wherein the first section of each of the wing structures of the pair of opposite, opposed wing structures and a portion of the upper surface of the lower wall form a cannula-retaining portion of the clip assembly;
wherein the clip assembly is configured to receive the portion of a cannula through an opening in an upper surface of the clip assembly and retain the cannula therein while the opening in the upper surface of the clip assembly remains open after receiving the portion of the cannula; and
wherein each first section includes a curve configured to correspond to an outer surface of the portion of the cannula, and wherein the clip assembly is configured such that, when the portion of the cannula is retained in the cannula-retaining portion, and when the wing structures are pushed downwards, the first sections move away from one another, thereby releasing the portion of the cannula.

18. The cannula fixation device of claim 17, the base comprising a rail assembly including a pair of opposite, opposed rails extending from the upper surface of the platform, each of the rails including a flange extending toward the other rail, wherein a portion of the base is configured to be slideably retained between the flanges and the upper surface of the platform, and wherein each flange includes a first notch defined therein and configured to receive a rail-engagement locking feature when the clip assembly is in the first position, and a second notch defined therein and configured to receive the rail-engagement locking feature when the clip assembly is in the second position.

* * * * *